United States Patent [19]

Bajusz et al.

[11] 4,288,432

[45] Sep. 8, 1981

[54] NOVEL ENKEPHALIN ANALOGS AND PROCESS FOR THE PREPARATION THEREOF

[75] Inventors: Sándor Bajusz; András Rónay; Jozsef Szekely, all of Budapest, Hungary

[73] Assignee: Richter Gedeon Vegyészeti Gyár Rt., Budapest, Hungary

[21] Appl. No.: 157,064

[22] Filed: Jun. 6, 1980

[30] Foreign Application Priority Data

Jun. 12, 1979 [HU] Hungary ............................... GO 1448

[51] Int. Cl.³ ...................... A61K 37/00; C07C 103/52
[52] U.S. Cl. ............................... 424/177; 260/112.5 R
[58] Field of Search ................... 260/112.5 R; 424/177

[56] References Cited

PUBLICATIONS

S. Bajusz et al., FEBS Letters, vol. 76, No. 1, 1977, pp. 91–92.

*Primary Examiner*—Delbert R. Phillips
*Attorney, Agent, or Firm*—Karl F. Ross

[57] ABSTRACT

The invention relates to novel enkephalin analoge of the general formula I

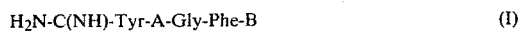

H$_2$N-C(NH)-Tyr-A-Gly-Phe-B    (I)

wherein
- Tyr, Gly and Phe stand for an L-tyrosine, glycine and L-phenylalanine residue, resp.
- A stands for a D-amino acid residue having a lower alkyl group or a lower thioalkyl group as side chain, and
- B stands for an amino group or an L-proline amide moiety, and their pharmaceutically acceptable salts. These compounds can be prepared from peptides containing terminal amino group corresponding in amino acid sequence by transforming the terminal amino group to guanidino group in a known way and, if desired, by forming a salt with a pharmaceutically acceptable acid.

The novel compounds of the general formula I possess valuable morphine-like (enkephalin-like) opiate activities.

6 Claims, No Drawings

NOVEL ENKEPHALIN ANALOGS AND PROCESS FOR THE PREPARATION THEREOF

This invention relates to novel enkephalin analogs having the formula I

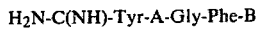
H₂N-C(NH)-Tyr-A-Gly-Phe-B    I wherein
Tyr, Gly and Phe, according to the literature [e.g. J. Biol. Chem. 247, 977 (1972)] are a L-tyrosine, glycine and L-phenylalanine residue, respectively,
A is a D-amino acid residue having a lower alkyl or lower thioalkyl group as side chain, and
B is an amino group of an L-proline amide moiety, and their pharmaceutically acceptable salts. Furthermore, the invention relates to a process for the preparation of these compounds.

It is known that the morphine-like (i.e. opioid) potencies of the two natural opioid peptides, methionine- and leucine-enkephalin [J. Hughes et al.: Nature 258, 577, (1975); structural formulae

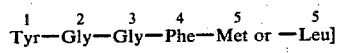
Tyr—Gly—Gly—Phe—Met or —Leu]

can be enhanced by substitution at positions 2 and 5. Thus, substituting D-methionine into position 2 and L-proline amide into position 5 can produce an enkephalin analog of the structure Tyr-D-Met-Gly-Phe-Pro-NH₂ which is one of the most powerful enkephalin analogs (Belgian Pat. No. 858,453).

The invention aims at preparing novel enkephalin analogs possessing higher opiate activity than that of the hitherto known derivatives.

Now it has been found that opiate activities of potent enkephalin analogs obtained by suitable amino acid substitution can be enhanced further by attaching an amidino group to the terminal amino group, i.e. by producing peptides containing a terminal guanidino group. The enhanced opiate activities of resulting new derivatives of formula I can be demonstrated in the conventional and generally accepted test systems, i.e. in guinea-pig ileum (GPI) [H. W. Kosterlitz and A. J. Watt: Br. J. Pharmacol. 33, 266 (1968); H. W. Kosterlitz et al.: Br. J. Pramacol. 39, 398 (1970)] and in mouse ves deferens (MVD) preparations [J. Hughes et al.: Br. J. Pharmacol. 53, 371 (1975)]. Table I shows the opioid activities of four peptides containing terminal guanidino group as compared to those of parent, amino-terminated analogs. The figures represent the activities of compounds relative to morphine (the activity of normorphine is taken as unity=1.0).

TABLE I

| Opiate Activities of derivatives of formula I and of the parent NH₂-terminated analogs as determined in guinea-pig ileum (GPI) and mouse vas deferens (MVD) preparations (opiate activity of normorphine = 1.0) | | | |
|---|---|---|---|
| PEPTIDES | GPI[a] | GPI[b] | MVD[c] |
| H-Tyr-D-Met-Gly-Phe-Pro-NH₂ | 8 | 8 | 8 |
| H₂N-C-(NH)-Tyr-D-Met-Gly-Phe-Pro-NH₂ | 825 | 173 | 25 |
| H-Tyr-D-Met-Gly-Phe-NH₂ | 17 | 17 | 4 |
| H₂N-C-(NH)-Tyr-D-Met-Gly-Phe-NH₂ | 211 | 79 | 21 |
| H-Tyr-D-Nle-Gly-Phe-NH₂ | 22 | 22 | 8 |
| H₂N-C-(NH)-Tyr-D-Nle-Gly-Phe-NH₂ | 126 | 79 | 18 |
| H-Tyr-D-Nle-Gly-Phe-Pro-NH₂ | 12 | 12 | 10 |
| H₂N-C-(NH)-Tyr-D-Nle-Gly-Phe-Pro-NH₂ | 79 | 21 | 17 |

TABLE I-continued

| Opiate Activities of derivatives of formula I and of the parent NH₂-terminated analogs as determined in guinea-pig ileum (GPI) and mouse vas deferens (MVD) preparations (opiate activity of normorphine = 1.0) | | | |
|---|---|---|---|
| PEPTIDES | GPI[a] | GPI[b] | MVD[c] |

[a]GPI assay according to Kosterlitz and Watt [Br.J. Pharmacol. 33, 266 (1968)]
[b]GPI assay according to Kosterlitz et al. [Br. J. Pharmacol. 39, 398 (1970)]
[c]MVD assay according to Hughes et al. [Br. J. Pharmacol. 53, 371 (1975)]

The positive result achieved by exchanging the N-terminal amino group of peptides for a guanidino moiety came as a surprise because this is the most vulnerable part of the enkephalin molecule; modification of terminal amino group (e.g. omission, acetylation or dialkylation), in general, results in a complete loss or at least marked reduction of the opiate activity [e.g. B. A. Morgan et al.: Communications J. Pharm. Pharmac. 28, 660 (1976)].

It is important to note that of the derivatives having formula I, those having an amino group as B possess higher analgesic activity than morphine upon systemic administration, too, as determined in the rat tail-flick test [F. E. D'Amour and D. L. Smith: J. Pharm. Ther. 72, 74 (1941)].

Accordingly, the invention relates to a process for the preparation of novel enkephalin analogs having the formula I, wherein Tyr, Gly, Phe, A and B have the same meaning as above, and also of their salts; said process comprises the step of transforming the terminal amino group of a peptide corresponding in amino acid sequence to a guanidino group in a known way and, if desired, forming a salt with a pharmaceutically acceptable acid.

The process according to the invention can be carried out advantageously by reacting a peptide corresponding in amino acid sequence with 1.1 to 2.0 equivalents of 1-amidino-3,5-dimethyl-pyrazole acetate in the presence of 1.1 to 2.0 equivalents of triethylamine in a solution of 1.0 to 1.1 mmoles/ml concentration using aqueous or water-free alkanol having a lower alkyl chain as solvent at 20°–80° C.; at the end of the reaction the solution is evaporated and the peptide containing the guanidino group at its N-terminus is isolated and, if desired, transformed into a salt with an acid.

The process of the invention is further illustrated by the following Examples.

In the Examples, the $R_f$ values were determined by thin-layer chromatography in silica gel (Kieselgel G, Reanal, Budapest) in the following solvent systems:
1. ethyl acetate-pyridine-acetic acid-water (480:20:6:11)
2. ethyl acetate-pyridine-acetic acid-water (240:20:6:11)
3. ethyl acetate-pyridine-acetic acid-water (60:20:6:11)
4. chloroform-methanol (9:1)
5. methylene chloride-25% aqueous ammonia-methanol (12:3:8)

EXAMPLE 1

Preparation of amidino-L-tyrosyl-D-methionyl-glycyl-L-phenylalanyl-L-proline amide (in formula I, A is an L-methionine residue and B represents the L-proline amide group).

1st step: 1-Amidino-3,5-dimethyl-pyrazole acetate
20.1 g (100 mmoles) of 1-amidino-3,5-dimethyl-pyrazole nitrate [J. Thiele and E. Dralle: Ann. 302, 294 (1898) are dissolved in 110 ml of 1 N sodium hydroxide and 200 ml of methylene chloride with stirring. The two phases are separated, the organic layer is dried on sodium sulphate, then 6 ml (100 mmoles) of acetic acid are added and the solution is evaporated under reduced pressure. The crystalline residue is suspended in diethyl ether, filtered, washed with diethyl ether and dried. Yield: 18.25 g (92%) of the desired product; Analysis: $C_8H_{12}O_2N_4$ (198.2) Calc: C 48.47%; H 7.12%; N 28.27%; Found: C 48.6%; H 7.1%; N 28.5%.

2nd step: Amidino-L-tyrosyl-D-methionyl-glycyl-L-phenylalanyl-L-proline amide acetate hydrate 1.45 g (2 mmoles) of L-tyrosyl-D-methionyl-L-phenylalanyl-proline amide acetate trihydrate (Belgian Pat. No. 858,453) and 0.5 g of 1-amidino-3,5-dimethyl-pyrazole acetate (1st step of Example 1) are dissolved in 2 ml of ethanol, then 0.4 ml (2.86 mmoles) of triethylamine is added and the mixture warmed at 60°–70° C. for 4 hours. Thereafter the reaction mixture is diluted with 30 ml of ethylacetate, the precipitate is filtered off, washed with ethyl acetate and dried in vacuum. Yield: 0.58 g (80%) of the desired product; $R_f^5$ 0.63–0.68; $[\alpha]_D^{20} = +4°$ (c=1, in 1 N acetic acid).

EXAMPLE 2

Preparation of amidino-L-tyrosyl-D-methionyl-glycyl-L-phenylalanine amide (in formula I, A is the D-methionine residue and B is the amino group).

1st step: Tert.butyloxycarbonyl-D-methionyl-glycyl-L-phenylalanine amide 5.35 g (15 mmoles) of benzyloxycarbonyl-glycyl-L-phenyl-alanine amide [J. S. Fruton and M. Bergmann: J. Biol. Chem. 145, 253 (1942)] dissolved in 100 ml of methanol are hydrogenated in the presence of a palladium-charcoal catalyst. At the end of the reaction the catalyst is filtered off, washed with methanol and the combined methanolic solutions are evaporated under reduced pressure. The thus-obtained glycyl-L-phenylalanine amide residue ($R_f^3$ 0.19–0.29), is dissolved together with 6.43 g (15 mmoles) of 2,4,5-trichlorophenyl tert.butyloxycarbonyl-D-methioninate (W. Broadbent et al.: J. Chem. Soc. 1967, 2632) in 30 ml of pyridine and allowed to stand overnight. The reaction mixture is evaporated and the residue is triturated with diethyl ether containing 1% of mercaptoethanol, then filtered off, washed with diethyl ether and dried. Yield: 5.1 g (75%) of the desired product; $R_f^2$ 0.70–0.77.

2nd step: D-Methionyl-glycyl-L-phenylalanine amide hydrochloride 4.52 g (10 mmoles) of protected tripeptide amide (1st step of Example 2) are suspended in 20 ml of ethyl acetate, then 40 ml of ethyl acetate containing 11–15% of hydrochloric acid are added with stirring while chilling in an ice bath. After an hour of stirring the reaction mixture is diluted with 60 ml of ethyl acetate, the precipitate is filtered off, washed with ethyl acetate and dried in a vacuum over potassium hydroxide. Yield: 3.7 g (95%) of the aimed product; $R_f^3$ 0.50–0.55.

3rd step: Tert.butyloxycarbonyl-L-tyrosyl-D-methionyl-glycyl-L-phenylalanine amide 1.4 g (5 mmoles) of tert.butyloxycarbonyl-L-tyrosine [G. W. Anderson and A. C. McGregor: J. Am. Chem. Soc. 79, 6180 (1957)] are dissolved in 10 ml of dimethylformamide and cooled to −15° C. At this temperature 0.6 ml (5 mmoles) of N-methyl-morpholine and 0.7 ml (5 mmoles) of isobutyl chloroformate are added with stirring, then, after 10 minutes, a suspension, prepared from 1.95 g (5 mmoles) of tripeptide amide hydrochloride (2nd step of Example 2) and 0.7 ml (5 mmoles) of triethylamine in 10 ml of dimethylformamide cooled to −15° C., is added. The reaction mixture is stirred at −15° C. for two hours and at 0° C. for one hour, then evaporated under reduced pressure. The residue is triturated with water, filtered, washed with water and dried, then crystallized from 30 ml of hot ethyl acetate. Yield: 2.15 g (70%) of the desired product; $R_f^1$ 0.64–0.68.

4th step: L-Tyrosyl-D-methionyl-glycyl-L-phenylalanine amide acetate hydrate 1.85 g (3 mmoles) of protected tetrapeptide amide (3rd step of Example 2) are suspended in 3 ml of ethyl acetate, and ethyl acetate containing 11 to 15% of hydrochloric acid are admixed with stirring under cooling. After stirring for an hour the reaction mixture is diluted with 20 ml of ethyl acetate, the precipitate is filtered off, washed with ethyl acetate and dried. The product thus obtained is dissolved in 10 ml of water and poured into an anion exchange resin in acetate cycle (AG 1×2, Bio-Rad, Richmond, Calif.). Resin is filtered off, washed with 80 ml of water, then the aqueous solutions are combined and lyophilized. Yield: 1.07 g (60%) of the desired product; $R_f^3$ 0.55–0.60; $R_f^5$ 0.89–0.97; $[\alpha]_D^{20} = +82°$ (c=1, in 1 N acetic acid).

5th step: Amidino-L-tyrosyl-D-methionyl-glycyl-L-phenylalanine amide acetate hydrate 0.6 g (1 mmole) of tetrapeptide amide acetate hydrate (4th step of Example 2) and 0.24 g (1.2 mmoles) of pyrazole derivative (1st step of Example 1) are dissolved in 2 ml of ethanol, then 0.2 ml (1.43 mmoles) of triethylamine are added and the reaction mixture is warmed at 60° C. for 5 hours. Thereafter the solution is concentrated under reduced pressure, then diluted with about 20 ml of ethyl acetate. The precipitate is filtered off, washed with ethyl acetate and dried, then dissolved in 10 ml of water and lyophilized. Yield: 0.5 g (80%) of the desired product; $R_f^3$ 0.54–0.59; $R_f^5$ 0.65–0.70; $[\alpha]_D^{20} = +4°$ (c=1, in 1 N acetic acid).

EXAMPLE 3

Preparation of amidino-L-tyrosyl-D-norleucyl-glycyl-L-phenylalanine amide (in formula I, A is a D-norleucine residue and B stands for an amino group)

1st step: Benzyloxycarbonyl-D-norleucyl-glycyl-L-phenylalanine amide 3.98 g (15 mmoles) of benzyloxycarbonyl-L-norleucine [N. Izumiya et al.: J. Chem. Soc. Japan 79, 420 (1958)] are dissolved in 15 ml of dimethylformamide and cooled to −15° C. At this temperature 1.7 ml (15 mmoles) of N-methylmorpholine and 2 ml (15 mmoles) of isobutyl chloroformate are added with stirring, then, after 10 minutes, a dimethylformamide solution prepared as described below. 5.35 g (15 mmoles) of benzyloxycarbonyl-glycyl-L-phenylalanine amide [J. S. Fruton and M. Bergmann: J. Biol. Chem. 145, 253 (1942)] dissolved in 100 ml of methanol are hydrogenated in the presence of a palladium-charcoal catalyst; at the end of the reaction the catalyst is filtered off, methanol is evaporated under reduced pressure and the residue is dissolved in 15 ml of dimethylformamide. The reaction mixture is stirred at −15° C. for two hours and at 0° C. for one hour. Thereafter the mixture is evaporated, the residue is triturated with water, filtered off and dried. The product thus obtained is crystallized from a mixture of ethyl acetate and petroleum ether. Yield: 5.0 g (70%) of the desired product; $R_f^2$ 0.75–0.80.

2nd step: D-Norleucyl-glycyl-L-phenylalaline amide hydrochloride 4.7 g/10 mmoles) of protected tripeptide amide (1st step of Example 3) are suspended in a mixture of 50 ml of ethanol and 50 ml of dimethylformamide, then 10 ml of 1 N hydrochloric acid added; the hydrogenation is carried out in the presence of a palladium-charcoal catalyst. At the end of the reaction catalyst is filtered off, washed with dimethylformamide and the combined solutions are evaporated under reduced pressure. The residue is triturated with ethyl acetate, filtered and washed with ethyl acetate. Yield: 3.05 g (82%) of the desired product; $R_f^3$ 0.45–0.55.

3rd step: Tert.butyloxycarbonyl-L-tyrosyl-D-norleucyl-glycyl-L-phenylalanine amide 1.4 g (5 mmoles) of tert.butyloxycarbonyl-L-tyrosine and 1.85 g (5 mmoles) of tripeptide amide hydrochloride (2nd step of Example 3) are coupled according to the procedure specified in the 3rd step of Example 2. Yield: 1.94 g (65%) of the desired product; $R_f^1$ 0.70–0.75.

4th step: L-Tyrosyl-D-norleucyl-glycyl-L-phenylalanine amide acetate hydrate

Starting with 1.8 g (3 mmoles) of protected tetrapeptide amide (3rd step of Example 3) the procedure specified in the 4th step of Example 2 is followed. Yield: 1.12 g (65%) of the desired product; $R_f^3$ 0.6–0.65; $R_f^5$ 0.90–0.95; $[\alpha]_D^{20} = +80.5°$ (c=1, in 1 N acetic acid).

5th step: Amidino-L-tyrosyl-D-norleucyl-glycyl-L-phenylalanine amide acetate hydrate Starting with 0.58 g (1 mmole) of tetrapeptide amide acetate hydrate (4th step of Example 3) the procedure specified in the 5th step of Example 2 is followed. Yield: 0.46 g (75%) of the desired product; $R_f^5$ 0.62–0.70; $[\alpha]_D^{20} = +40.5°$ (c=1, in 1 N acetic acid).

EXAMPLE 4

Preparation of amidino-L-tyrosyl-D-norleucyl-glycyl-L-phenylalanyl-L-proline amide (in formula I, A is a D-norleucine residue and B is an L-proline amide group)

1st step: Benzyloxycarbonyl-D-norleucyl-glycyl-L-phenylalanyl-L-proline 7.95 g (30 mmoles) of benzyloxycarbonyl-D-norleucine [N. Izumiya et al.: J. Chem. Soc. Japan 79, 420 (1958)] and 5.95 g (30 mmoles) of 2,4,5-trichlorophenol are dissolved in 60 ml of ethyl acetate and cooled in ice bath. 5.8 g (28 mmoles) of dicyclohexylcarbodiimide are added to the cooled solution. After 2 hours the dicyclohexylurea precipite is filtered off, the solution is concentrated under reduced pressure and the residue is crystallized with n-hexane, filtered, washed with n-hexane and dried. The activated ester thus obtained (9.35 g; 75%; $R_f^4$ 0.82–0.92) is dissolved in 40 ml of pyridine, then 6.4 g (20 mmoles) of glycyl-L-phenylalanyl-L-proline (Belgian Pat. No. 858,453 and 2.8 ml (20 mmoles) of triethylamine are added. The reaction mixture is stirred at room temperature overnight, then evaporated, the residue is dissolved in 50 ml of diethyl ether and 50 ml of 5% sodium hydrogen carbonate. The aqueous layer is washed with 2×30 ml of diethyl ether, then acidified with 1 N sulphuric acid to pH 3. The product separated is extracted with 3×50 ml of ethyl acetate; the combined ethyl acetate solutions are washed with 2×20 ml of water, then, after drying over sodium sulphate, evaporated under reduced pressure. The residue is triturated with cyclohexane, filtered, washed with cyclohexane and dried. Yield: 9.97 g (88%) of the desired product; $R_f^2$ 0.28–0.38.

2nd step: Benzyloxycarbonyl-D-norleucyl-glycyl-L-phenylalanyl-L-proline amide 8.5 g (15 mmoles) of protected tetrapeptide (1st step of Example 4) are dissolved in 30 ml of tetrahydrofurane and cooled to −15° C. At this temperature 1.7 g (15 mmoles) of N-methyl-morpholine and 2.0 ml (15 mmoles) of isobutyl chloroformate are admixed with stirring, then, after 10 minutes, 8 ml of cold (below 5° C.) 20–25% ammonia are added. Stirring is continued at 0° C. for an hour and tetrahydrofurane is distilled off from the reaction mixture under reduced pressure. 20 ml of water and 50 ml of ethyl acetate are added to the residue, then the layers are separated. The aqueous layer is extracted with 20 ml of ethyl acetate, and the combined ethyl acetate solutions are washed with 3×20 ml of water, then, after drying over sulphate, evaporated under reduced pressure. The residue is triturated with diethyl ether, filtered, washed with diethyl ether and dried. Yield: 9.3 g (91%) of the desired product; $R_f^2$ 0.4–0.5.

3rd step: D-Norleucyl-glycyl-L-phenylalanyl-L-proline amide 5.66 g (10 mmoles) of protected tetrapeptide amide (2nd step of Example 4) are dissolved in 100 ml of methanol and hydrogenated in the presence of a palladium-charcoal catalyst. At the end of the reaction the catalyst is removed by filtration, washed with methanol and the combined methanolic solutions are evaporated under reduced pressure. The residue is triturated with diethyl ether, filtered, washed with diethyl ether and dried. Yield: 3.7 g (85%) of the desired compound; $R_f^3$ 0.38–0.48.

4th step: Tert.butyloxycarbonyl-L-tyrosyl-D-norleucyl-glycyl-L-phenylalanyl-L-proline amide 1.4 g (5 mmoles) of tert.butyloxycarbonyl-L-tyrosine and 2.16 g (5 mmoles) of tetrapeptide amide (3rd step of Example 4) are condensed according to the procedure specified in the 3rd step of Example 2 with the difference that no triethylamine is added. Yield: 3.0 g (86%) of the desired product; $R_f^1$ 0.4–0.5.

5th step: L-Tyrosyl-D-norleucyl-glycyl-L-phenylalanyl-L-proline amide acetate hydrate Starting with 2.1 g (3 mmoles) of protected pentapeptide amide the procedure specified in the 4th step of Example 2 is followed. Yield: 1.45 g (72%) of the desired product; $R_f^3$ 0.47–0.52; $R_f^5$ 0.92–0.98; $[\alpha]_D^{20} = +26°$ (c=1, in 1 N acetic acid).

6th step: Amidino-L-tyrosyl-D-norleucyl-glycyl-L-phenylalanyl-L-proline amide acetate hydrate On starting with 0.7 g (1 mmole) of pentapeptide amide acetate hydrate (5th step of Example 4) the procedure specified in the 5th step of Example 2 is followed. Yield: 0.57 g (80%) of the desired product; $R_f^3$ 0.33–0.43; $R_f^5$ 0.65–0.75; $[\alpha]_D^{20} = +1°$ (c=1, in 1 N acetic acid).

We claim:

1. An enkephalin analog having the formula I

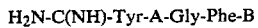  (I)

wherein
Tyr, Gly and Phe are L-Tyrosine, glycine and L-phenylalanine residues, respectively,
A is a D-amino acid residue having a lower alkyl group of a lower thioalkyl group as a side chain, and
B is an amino group of an L-proline amide moiety, or a pharmaceutically acceptable salt thereof.

2. An enkephalin analog or salt of the formula I as defined in claim 1, in the form of a physiologically acceptable salt.

3. An analgesic composition containing an analgesically effective amount of a compound of the formula I as active ingredient as defined in claim 1 or a physiologically acceptable salt thereof, prepared with a pharmaceutically acceptable carrier, diluent and/or auxiliary agent.

4. The compound defined in claim 1 which is selected from the group consisting of:

$H_2N$-C(NH)-Tyr-D-Met-Gly-Phe-Pro-$NH_2$,
$H_2N$-C(NH)-Tyr-D-Met-Gly-Phe-$Nh_2$,
$H_2N$-C(NH)-Tyr-D-Nle-Gly-Phe-Pro-$NH_2$, and
$H_2N$-C(NH)-Tyr-D-Nle-Gly-Phe-$NH_2$.

5. The compound defined in claim 4 which is $H_2N$-C(NH)-Tyr-D-Met-Gly-Phe-Pro-$NH_2$.

6. An analgesic method of treatment which comprises the step of administering to an animal requiring analgesic treatment a pharmaceutically effective amount of the compound of the formula I as defined in claim 1 or a pharmaceutically acceptable salt thereof.

* * * * *